(12) United States Patent
Usuelli et al.

(10) Patent No.: US 11,452,680 B2
(45) Date of Patent: Sep. 27, 2022

(54) LIQUIDS HAVING OIL-IN-WATER SELF-EMULSIFYING PROPERTIES, COMPOSITIONS, USES AND METHODS RELATING TO SAME

(71) Applicant: INNOVACOS CORP., Mt Arlington, NJ (US)

(72) Inventors: Fabio Usuelli, Besana in Brianza (IT); Alain Thibodeau, St-Augustin-de-Desmaures (CA)

(73) Assignee: INNOVACOS CORP., Mt. Arlington, NJ (US)

( * ) Notice: Subject to any disclaimer, the term of this patent is extended or adjusted under 35 U.S.C. 154(b) by 35 days.

(21) Appl. No.: 16/662,735

(22) Filed: Oct. 24, 2019

(65) Prior Publication Data
US 2020/0129397 A1    Apr. 30, 2020

Related U.S. Application Data

(60) Provisional application No. 62/751,043, filed on Oct. 26, 2018.

(51) Int. Cl.
| | |
|---|---|
| *A61K 8/34* | (2006.01) |
| *A61K 8/9794* | (2017.01) |
| *A61K 8/9789* | (2017.01) |
| *A61K 8/06* | (2006.01) |
| *A61K 8/36* | (2006.01) |
| *A61K 8/37* | (2006.01) |
| *A61K 8/86* | (2006.01) |
| *A61Q 19/00* | (2006.01) |

(52) U.S. Cl.
CPC .............. *A61K 8/345* (2013.01); *A61K 8/062* (2013.01); *A61K 8/361* (2013.01); *A61K 8/375* (2013.01); *A61K 8/86* (2013.01); *A61K 8/9789* (2017.08); *A61K 8/9794* (2017.08); *A61Q 19/007* (2013.01)

(58) Field of Classification Search
None
See application file for complete search history.

(56) References Cited

U.S. PATENT DOCUMENTS

| | | | |
|---|---|---|---|
| 4,454,113 A | 6/1984 | Hemker | |
| 4,719,103 A | 1/1988 | Krevald et al. | |
| 9,827,186 B2 | 11/2017 | Thibodeau | |
| 10,195,123 B2 | 2/2019 | Thibodeau | |
| 2007/0092470 A1 | 4/2007 | Allef et al. | |
| 2007/0166270 A1 | 7/2007 | Neuss et al. | |
| 2007/0178144 A1 | 8/2007 | Hameyer et al. | |
| 2007/0270336 A1 | 11/2007 | Denda et al. | |
| 2012/0035130 A1 | 2/2012 | Peter et al. | |
| 2018/0036218 A1* | 2/2018 | Gu | A61K 9/107 |

FOREIGN PATENT DOCUMENTS

| | | |
|---|---|---|
| CA | 2469174 A1 | 1/2005 |
| CA | 2943423 C | 8/2019 |
| CA | 2896617 C | 9/2020 |
| DE | 102006033845 A1 | 1/2005 |
| EP | 2213336 A2 | 8/2010 |
| EP | 2213336 A3 | 6/2015 |
| EP | 2925290 B1 | 5/2018 |
| JP | H1095749 * | 4/1998 |
| WO | 9904749 A2 | 2/1999 |
| WO | 2012120290 A2 | 9/2012 |
| WO | 2012120290 A3 | 9/2012 |

OTHER PUBLICATIONS

JPH1095749 translated doc (Year: 1998).*
DE102006033845A1 to Rossing et al. English translation.
EP14760625.5 Supplementary European Search Report dated Mar. 18, 2016; 7 pages.
EP19205505.1 Supplementary European Search Report dated Mar. 25, 2020; 9 pages.
Happi website (Sep. 2010) Formulating natural products; 5 pages.
Innovacos Technical Data Sheet on Polyaquol Apr. 2013.
International Preliminary Report on Patentability issued in PCTCA2014050182 dated Sep. 17, 2015.
International Preliminary Report on Patentability issued in PCTCA2015050335 dated Nov. 3, 2016.
International Search Report and Written Opinion issued in PCTCA2014050182 dated Jun. 17, 2014.
International Search Report and Written Opinion issued in PCTCA2015050335 dated Jul. 17, 2015.
Liebert "Final report on the safety assessment of stearyl alcohol, oleyl alcohol and octyl dodecanol" Journal of the American College of Toxicology, 4(5), 1985, pp. 1-29.
WO199904749A2 English translation.
WO2016080270A1 English translation.

* cited by examiner

*Primary Examiner* — Terry A McKelvey
*Assistant Examiner* — Jacob A Boeckelman

(57) ABSTRACT

The present disclosure provides an oil-in-water (O/W) emulsifier comprising esters of polyglycerol-6 and of fatty acids, and of polyglycerol-X, wherein X is any one of 4, 5 and 7 to 12 and of fatty acids, wherein the fatty acids are liquid fatty acids having a purity of at least 85% w/w, wherein the polyglycerols have a purity of at least 60% w/w, and wherein the emulsifier can form a stable O/W emulsion for at least 1 week at about 50° C. It also provides a method for making the emulsifier and emulsions comprising the emulsifier.

23 Claims, 2 Drawing Sheets

LIQUIDS HAVING OIL-IN-WATER SELF-EMULSIFYING PROPERTIES, COMPOSITIONS, USES AND METHODS RELATING TO SAME

CROSS REFERENCE TO RELATED APPLICATIONS

This application claims benefit, under 35 U.S.C. § 119(e), of U.S. provisional application Ser. No. 62/751,043, filed on Oct. 26, 2018. The document above is incorporated herein in its entirety by reference.

STATEMENT REGARDING FEDERALLY SPONSORED RESEARCH OR DEVELOPMENT

N.A.

FIELD OF THE DISCLOSURE

The present disclosure relates to liquids having oil-in-water self-emulsifying properties. More specifically, the liquids comprise combinations of polyglyceryl fatty acid esters.

BACKGROUND OF THE DISCLOSURE

An emulsion consists of two immiscible liquids mixed together with small droplets of one liquid dispersed in the other liquid. The dispersion is usually not stable and all the droplets "clump" together over time to form two layers. An emulsion can be stabilized by inhibiting coalescence (i.e., preventing the droplets from clumping together) by the presence of surfactant molecules. The majority of emulsions can be classified according to the chemical nature of the liquids, such as oil-in-water (O/W) or water-in-oil (W/O).

O/W emulsions are widely used for topical formulations due to their sensorial profile characterized by light skin feel, non-greasy texture, and high spreadability index, as well as for their easy production methods.

Polyglycerols esterified with short (e.g., C10 to C14) fatty acid chains are dense liquids very often presenting lack of homogeneity, phase separation problems (unreacted polyglycerol etc.) and formation of precipitates due to cyclized or concatenated polyglycerols. They are known to usually have lower emulsifying properties and stability for O/W emulsions when compared to long fatty acid chain/polyglycerol esters. The use of warm rooms or mechanical mixing procedures to homogenize products before their use becomes necessary, which complicates the formulation process and results in costlier methods. They are not used as primary emulsifiers for such reasons. While despite those difficulties, polyglycerol esters with short fatty acid chains can be used as co-emulsifiers or solubilizers for topical uses, they need to be complemented with stabilizers or other additives to achieve stable emulsions.

While polyglycerols esterified with long (e.g., C18-C22) fatty acid chains generally result in a homogeneous product, they are in a solid physical state (i.e. waxes). As such they require heating to be melted before they can be homogenized or emulsified with other ingredients. The use of elevated temperatures during formulation processes may represent a problem especially when working with thermolabile active ingredients. Furthermore, having to pre-melt raw materials prior to their use increases the manufacturing cost.

There is a need for stable and efficient emulsifiers. There is also a need for a process for making emulsifiers reducing the need for heating and/or homogenizing steps.

Further, there is a need for liquid emulsifiers made of polyglycerol esters with fatty acids that do not require ionic surfactants or a non-ionic ethoxylated/propoxylated product for producing a stable emulsion. The presence of ionic surfactants can lead to skin sensitization and skin irritation, and the presence of acrylate polymers, ethoxylated and propoxylated products are not desirable to produce "green" (environmentally-friendly) emulsions. Thus, there is a need for O/W emulsions lacking ionic surfactants, acrylate polymers, ethoxylated or propoxylated emulsifiers.

SUMMARY OF THE DISCLOSURE

The present disclosure also presents a liquid having O/W self-emulsifying properties that are superior to that of other products found in prior art that can be used in cold process emulsification, and that can be used a single emulsifier, without ionic surfactants or a non-ionic ethoxylated/propoxylated product. The emulsifiers of the present disclosure may have a large range of viscosities (between about 100 to 20000 cPs). The lower end of this range is particularly advantageous from about 100 to about 1200 cPs in that it enables their use in formulations requiring a high fluidity such as e.g., serums and sprays (a g., sunscreen lotions).

In specific embodiments, the emulsifier comprises polyglycerol-6 esterified with a fatty acid chain (e.g., C8-C14 fatty acid) that is liquid at room temperature and polyglycerol-X, wherein X is any integer from 4-5 and 7-12, (i.e. "pure polyglycerol-4", "pure polyglycerol-5", "pure polyglycerol-7", "pure polyglycerol-8", "pure polyglycerol-9", "pure polyglycerol-10", "pure polyglycerol-11" or "pure polyglycerol-12") also esterified with a C8-C14 fatty acid. In specific embodiments, the emulsifier of the instant disclosure is a dense liquid.

The present disclosure shows that the emulsifier described herein procures increased oil in water (O/W) emulsion stability compared to (1) when the same polyglycerols are esterified separately and then combined; (2) when each esterified polyglycerol is used separately; and (3) when corresponding commercially available PGs and fatty acids are used.

Also disclosed herein is a process for making the emulsifiers disclosed herein. Such process enables the generation of an emulsifier with a pre-determined polarity index and enables a modulation of the polarity index of the generated emulsifier depending on its intended use. For example, its ability to solubilize compounds can be increased by using longer polyglycerols in compositions of the present disclosure. Hence, without being so limited, the emulsifier disclosed herein made of PG6-fatty acid and PG10-fatty acid esters can be used not only as an emulsifier but also as a solubilizer.

In specific embodiment, the emulsifier disclosed herein is further able to produce O/W emulsions in absence of other co-emulsifiers or stabilizers and based on its liquid physical state. In specific embodiments, the emulsifier disclosed herein can also be used for cold process emulsification (i.e. without a heating step (e.g., in ovens) or the use warm rooms). In specific embodiments, the emulsifier disclosed herein can be used to form emulsions without (the need for) a pre-mixing step such as with mechanical agitation.

More specifically, in accordance with the present disclosure, there is provided the following items:

Item 1. An oil-in-water (O/W) emulsifier comprising esters of polyglycerol-6 and of a C12-C14 fatty acid, and of polyglycerol-X, wherein X is any one of 4, 5 and 7 to 12 and of the C12-C14 fatty acid,
   wherein prior to mixing the C12-C14 fatty acid with the polyglycerols, the C12-C14 fatty acids has a purity of at least 85% w/w, and the polyglycerols have a purity of at least 60% w/w, and
   wherein the emulsifier can form a stable O/W emulsion for at least 1 week at about 50° C., and is liquid at about 20° C. to about 30° C.

Item 2. The emulsifier of item 1, wherein the esters were prepared by mixing the polyglycerol-6 and the polyglycerol-X prior to, or during esterification with the fatty acid.

Item 3. The emulsifier of items 1 or 2, wherein the polyglycerol-X is a polyglycerol-4 and wherein the ratio of polyglycerols in the emulsifier is:
   (i) about 35 to about 45 parts of the polyglycerol-6; for
   (ii) about 55 to about 65 parts of the ester of the polyglycerol-4.

Item 4. The emulsifier of item 3, wherein the ratio of polyglycerols in the emulsifier is:
   (i) about 40 parts of the ester of the polyglycerol-6; for
   (ii) about 60 parts of the ester of the polyglycerol-4.

Item 5. The emulsifier of item 3 or 4, wherein the polyglycerol-4 has a purity of at least 70% w/w.

Item 6. The emulsifier of item 1 or 2, wherein the polyglycerol-X is a polyglycerol-10 and wherein the ratio of polyglycerols in the emulsifier is:
   (i) about 25 to about 35 parts of the ester of the polyglycerol-6; for
   (ii) about 65 to about 75 parts of the ester of the polyglycerol-10.

Item 7. The emulsifier of item 6, wherein the ratio of polyglycerols in the emulsifier is:
   (i) about 30 parts of the ester of the polyglycerol-6; for
   (ii) about 70 parts of the ester of the polyglycerol-10.

Item 8. The emulsifier of item 6 or 7, wherein the polyglycerol-10 has a purity of at least 65% w/w.

Item 9. The emulsifier of any one of items 1 to 8, wherein the fatty acid has a length of 010 to C14.

Item 10. The emulsifier of item 9, wherein the fatty acid has a length of C12.

Item 11. The emulsifier of item 10, wherein the fatty acid is lauric acid.

Item 12. The emulsifier of any one of items 1 to 11, wherein the fatty acid has a purity of at least 98% w/w.

Item 13. The emulsifier of any one of items 1 to 12, wherein the emulsifier comprises between about 0.9 and about 1.5 equivalent fatty acid for about 1 equivalent polyglycerol.

Item 14. The emulsifier of item 13, wherein the emulsifier comprises about 1.0 equivalent fatty acid for about 1.0 equivalent polyglycerol.

Item 15. The emulsifier of any one of items 1 to 14, wherein the emulsifier is present in an o/w emulsion.

Item 16. The emulsifier of item 15, wherein the emulsion does not comprise a co-emulsifier, a polar or an ionic surfactant, an ethoxylated product, a propoxylated product, a rheological modifier, a gelling agent, or any combination thereof.

Item 17. The emulsifier of item 15 or 16, wherein the emulsion is a cosmetic liquid composition.

Item 18. The emulsifier of any one of items 15 to 17, wherein the emulsion has a viscosity between 100 and 1200 cPs.

Item 19. A method of preparing an oil-in-water (O/W) emulsifier comprising:
   (a) heating polyglycerol-6, polyglycerol-X, wherein X is any one of 4, 5 and 7 to 12, and a C12-C14 fatty acid at about 70° C. to about 110° C. to form a mixture, wherein prior to mixing the C12-C14 fatty acid with the polyglycerols, the polyglycerols have a purity of at least 60% w/w, and the C12-C14 fatty acid has a purity of at least 85% w/w; and
   (b) esterifying the mixture at a temperature between about 120 and about 170° C.

Item 20. The method of item 19, wherein the polyglycerol-X is a polyglycerol-4 and wherein the ratio of polyglycerols in (a) is:
   (i) about 35 to about 45 parts of the polyglycerol-6; for
   (ii) about 55 to about 65 parts of the ester of the polyglycerol-4.

Item 21. The method of item 19, wherein the ratio of polyglycerols in (a) is:
   (i) about 40 parts of the ester of the polyglycerol-6; for
   (ii) about 60 parts of the ester of the polyglycerol-4.

Item 22. The method of item 20 or 21, wherein the polyglycerol-4 has a purity of at least 70% w/w.

Item 23. The method of item 20 or 21, wherein the polyglycerol-X is a polyglycerol-10 and wherein the ratio of polyglycerols in (a) is:
   (i) about 25 to about 35 parts of the ester of the polyglycerol-6; for
   (ii) about 65 to about 75 parts of the ester of the polyglycerol-10.

Item 24. The method of item 23, wherein the ratio of polyglycerols in the emulsifier is:
   (i) about 30 parts of the ester of the polyglycerol-6; for
   (ii) about 70 parts of the ester of the polyglycerol-10.

Item 25. The method of item 23 or 24, wherein the polyglycerol-10 has a purity of at least 65% w/w. Item 26. The method of any one of items 19 to 25, wherein the fatty acid has a length of C10 to C14.

Item 27. The method of item 26, wherein the fatty acid has a length of C12.

Item 28. The method of item 27, wherein the fatty acid is lauric acid.

Item 29. The method of any one of items 19 to 28, wherein the fatty acids have a purity of at least 98% w/w.

Item 30. The method of any one of items 19 to 29, wherein there is between about 0.9 and about 1.5 equivalent fatty acids for about 1 equivalent polyglycerol in the mixture.

Item 31. The method of any one of items 19 to 29, wherein there is about 1.0 equivalent fatty acid for about 1.0 equivalent polyglycerol in the mixture.

Other objects, advantages and features of the present disclosure will become more apparent upon reading of the following non-restrictive description of specific embodiments thereof, given by way of example only with reference to the accompanying drawings.

DESCRIPTION OF ILLUSTRATIVE EMBODIMENTS

Figure 1:
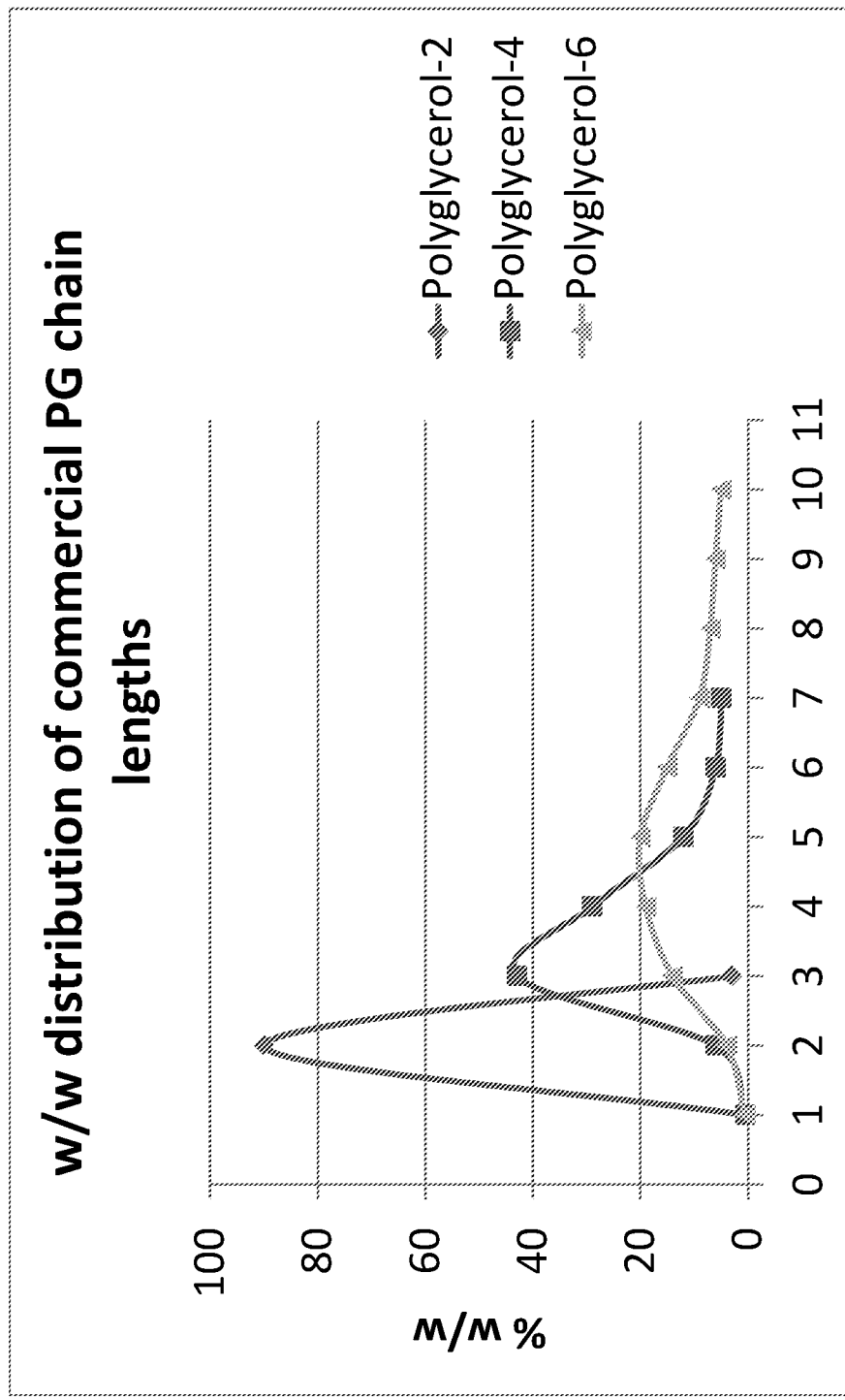
FIG. 1 shows the gaussian distribution of commercially available of polyglycerols-2, -4 and -6.

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

In the present description, a number of terms are extensively utilized. In order to provide a clear and consistent understanding of the specification and claims, including the scope to be given such terms, the following definitions are provided.

General Definitions

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the term "consists of" or "consisting of" means including only the elements, steps, or ingredients specifically recited in the particular claimed embodiment or claim.

By "pharmaceutically acceptable," "physiologically tolerable," "dermatologically acceptable", or "pharmaceutically suitable", "physiologically suitable," "dermatologically suitable" and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable", "cosmetically suitable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, horse, etc.

As used herein, the term "treat" or "treating" a subject having a disorder refers to subjecting the subject to a regimen, e.g., the administration of a composition of the present disclosure such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

In one aspect, the present disclosure relates to a liquid having oil-in-water (O/W) emulsion-forming properties. The liquid comprises two principal components: (a) a polyglyceryl-6 fatty acid ester; (b) a fatty acid ester of polyglycerol-X, wherein X is any integer from 4-5 and 7-12. Each of these components interacts with each other to confer advantages properties (e.g., self-emulsification, stability, homogeneity, etc.) to the liquids of the present disclosure and compositions (e.g., emulsions) produced therefrom.

As used herein, the term "polyglyceryl fatty acid ester" encompasses the terms "polyglyceryl-6 fatty acid ester" and "polyglyceryl-X fatty acid ester, wherein X is any integer from 4-5 and 7-12" and includes corresponding polyglycerol esters of fatty acids, as well as derivatives, variants and/or analogs of these compounds (e.g., relatively minor chemical/structural modifications of the corresponding polyglyceryl fatty acid esters) that do not significantly affect the ability of the liquid of the present disclosure to form a stable, self-emulsifying O/W composition.

As used herein, "stable" refers to a system (e.g., an emulsion) that exhibits no perceptible phase separation, or change in texture for a fixed period of time at a given temperature. An increase in stability includes herein any one of a reduction of phase separation, reduction of heterogeneity of texture and/or appearance (increase in homogeneity of texture and/or appearance) and reduction of precipitation. In some embodiments, an emulsion or gel of the present disclosure remains stable for at least 1 day, 2 days, 1 week, 2 weeks, 3 weeks, 1 month, or 5 weeks at about 50° C. In some embodiments, an emulsion of the present disclosure remains stable for at least 1 month at about 50° C.

In some embodiments, the liquids of the present disclosure have self-emulsifying properties. As used herein, "self-emulsifying" or "auto-emulsifying" refers to the ability to form a stable system or emulsion (e.g., O/W emulsion) in the context of the present disclosure without the need of adding another substance (e.g., a further emulsifier or co-emulsifier, hydrophilic polymer, polar surfactant, rheological modifier, gelling agent or other stabilizing agent), other than the polyglyceryl-6 fatty acid ester and polyglyceryl-X fatty acid ester, wherein X is any integer from 4-5 and 7-12, comprised in the liquids of the present disclosure.

In some embodiments, liquids and other compositions of the present disclosure can form O/W emulsions in the absence of an ionic surfactant, an ethoxylated product, a propoxylated product, a rheological modifier, or a gelling agent. In some embodiments, liquids and other compositions of the present disclosure do not comprise an ionic surfactant, an ethoxylated product, a propoxylated product, a rheological modifier, or a gelling agent. As used herein, "ethoxylated or propoxylated products" can include ethoxylated or propoxylated fatty alcohols, fatty acids, fatty amines, or other compounds produced by ethoxylation or propoxylation.

The mixture of polyglyceryl-6 fatty acid ester and polyglyceryl-X fatty acid ester, wherein X is any integer from 4-5 and 7-12 of the present disclosure, is liquid at room temperature (about 20° C. to about 30° C.). In specific embodiments, each fatty acid is a C8 to C14 fatty acids that is saturated or unsaturated, straight or branch chained substituted or unsubstituted or is C16 to C18 fatty acid that is unsaturated (e.g., monounsaturated) and may be straight or branch chained, substituted or unsubstituted. Hence, while fatty acids chains of the instant disclosure are optimally saturated to reduce the likelihood of oxidation, they may also be unsaturated (e.g., myristoleic acid (C14), palmitoleic acid (C16), oleic acid (C18), etc.). In some embodiments, one or more of the fatty chain lengths can be 12.

In some embodiments, the polyglyceryl-6 fatty acid ester and polyglyceryl-X fatty acid ester, wherein X is any integer representing the number of glycerol monomeric units, namely any one of 4-5 and 7-12, can comprise a mixture of fatty chain lengths (e.g., C10 and C12).

Fatty acid chains for use in the emulsifiers disclosed herein include, for example, saturated fatty acids such as caprylic acid (C8), pelargonic acid (C9), capric acid (C10), undecylic acid (C11), lauric acid (C12), tridecylic acid (C13), and myristic acid (C14); and unsaturated fatty acids such as palmitoleic acid (016:1), oleic acid (018:1), etc.

It would be understood by the skilled person that a preparation of a specific fatty acid having a given carbon chain length (e.g., when the preparation is obtained/purified from natural sources) may contain fatty acid species having other carbon chain lengths present to a lesser degree. Accordingly as used herein, reference to an individual fatty acid species (e.g., having a particular carbon chain length, or derived from a particular fatty acid such as capric, undecylic, lauric, tridecylic and myristic acid) is meant to refer to the main species of fatty acid that is found in the given preparation, but does not necessarily exclude the presence of other fatty acids in significantly less relative amounts.

In some embodiments, liquids of the present disclosure can comprise: (i) about 35 to about 45 parts (e.g., % w/w) of the polyglyceryl-6 fatty acid ester; and (ii) about 55 to about 65 parts of the polyglyceryl-4 fatty acid ester. In some embodiments, the emulsifier comprises about 36 to about 44 parts (preferably between about 37 to about 43 parts, more preferably about 40 parts) of the polyglyceryl-6 fatty acid ester. In some embodiments, liquids of the present disclosure can comprise about 35, 36, 37, 38, 39, 40, 41, 42, 43, 44 or 45 parts of the polyglyceryl-6 fatty acid ester. In some embodiments, liquids of the present disclosure can comprise the polyglyceryl-4 fatty acid ester in a range of about 56 to about 64 parts (preferably between about 57 to about 63 parts, more preferably about 60 parts). In some embodiments, liquids of the present disclosure can comprise about 55, 56, 57, 58, 59, 60, 61, 62, 63, 64 or 65 parts of the polyglyceryl-4 fatty acid ester. As used herein, "parts" refers to weigh ratios (i.e., parts-by-weight).

In some embodiments, liquids of the present disclosure can comprise: (i) about 25 to about 35 parts (e.g., % w/w) of the polyglyceryl-6 fatty acid ester; and (ii) about 65 to about 75 parts of the polyglyceryl-10 fatty acid ester. In some embodiments, the emulsifier comprises about 26 to about 34 parts (preferably between about 27 to about 33 parts, more preferably about 30 parts) of the polyglyceryl-6 fatty acid ester. In In some embodiments, liquids of the present disclosure can comprise about 25, 26, 27, 28, 29, 30, 31, 32, 33, 34 or 35 parts of the polyglyceryl-6 fatty acid ester. In some embodiments, liquids of the present disclosure can comprise the polyglyceryl-10 fatty acid ester in a range of about 66 to about 74 parts (preferably between about 67 to about 73 parts, more preferably about 70 parts). In some embodiments, liquids of the present disclosure can comprise about 65, 66, 67, 68, 69, 70, 71, 72, 73, 74 or 75 parts of the polyglyceryl-10 fatty acid ester.

In some embodiments, the polyglyceryl-6 fatty acid ester can be polyglyceryl-6 laurate, the polyglyceryl-10 fatty acid ester can be polyglyceryl-10 laurate, and the polyglyceryl-4 fatty acid ester can be polyglyceryl-4 laurate.

As used herein the term "pure" in the context of and polyglycerol-X, wherein X is any integer from 4-5 and 7-12, is a purity higher than that of the commercially available corresponding PG (i.e., a purity higher than that of commercially available PG4, PG5 an PG7 toPG12, hereinafter "pure polyglycerol-4", "pure polyglycerol-5", "pure polyglycerol-7", "pure polyglycerol-8", "pure polyglycerol-10", or "pure polyglycerol-12")).

Polyglycerols may be synthesized by well-known methods in the art including self-polymerization (homo-polymerization) of pure glycerol. Glycerol may be extracted from natural sources such as plant or animal oils or fats. PGs are also commonly available from multiple commercial sources.

Commercially available polyglycerols generally comprise a mixture of polyglycerols or various lengths. Commercial grades of polyglycerol-4 usually has the composition shown in the table immediately below, the major component being polyglycerol-3, and polyglycerol-4 generally constituting between 25-30% w/w of the mixture.

Commercial grade polyglycerol-6 is generally a mixture of polyglycerols with a minimum % of PG6 of 15% wlw, and commercial grade polyglycerol-10, a mixture of polyglycerols with a minimum % of PG10 of 10% wlw. The Gaussian distribution of commercial grades of polyglycerols-2, -4 and -6 is exemplified in FIG. 1.

In a specific embodiment, "pure polyglycerol-X", wherein X is any integer from 4 to 12, refers to a purity of more than 35% w/w, or more than 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75% w/w, etc. In a specific embodiment, it refers to a purity of more than 60% w/w. More specifically, in the context of "pure PG6", it refers to a purity higher than that of commercially available PG6 (e.g., >35, 40, 45, 50, 55% w/w, etc.). In a specific embodiment, it refers to a purity of >60% w/w, and preferably >65%w/w. In the context of "pure PG4", it refers to a purity higher than that of commercially available PG4 (e.g., >35, 40, 45, 50, 55% w/w, etc.). In a specific embodiment, it refers to a purity of >60% w/w, preferably >65% w/w, more preferably >70% w/w. In the context of "pure PG10", it refers to a purity higher than that of commercially available PG4 (e.g., >35, 40, 45, 50, 55% w/w, etc.). In a specific embodiment, it refers to a purity of >60% w/w, preferably >65% w/w.

Polyglycerols of the instant disclosure also advantageously display a sharp length distribution peak when compared with corresponding commercially available ones. For example, pure PG4 advantageously contains less than 15% w/w each of PG3 and PG5, pure PG6 advantageously contains less than 15% w/w each of PG5 and PG7, and pure PG10 advantageously contains less than 15% w/w each of PG9 and PG11.

Figure 2:
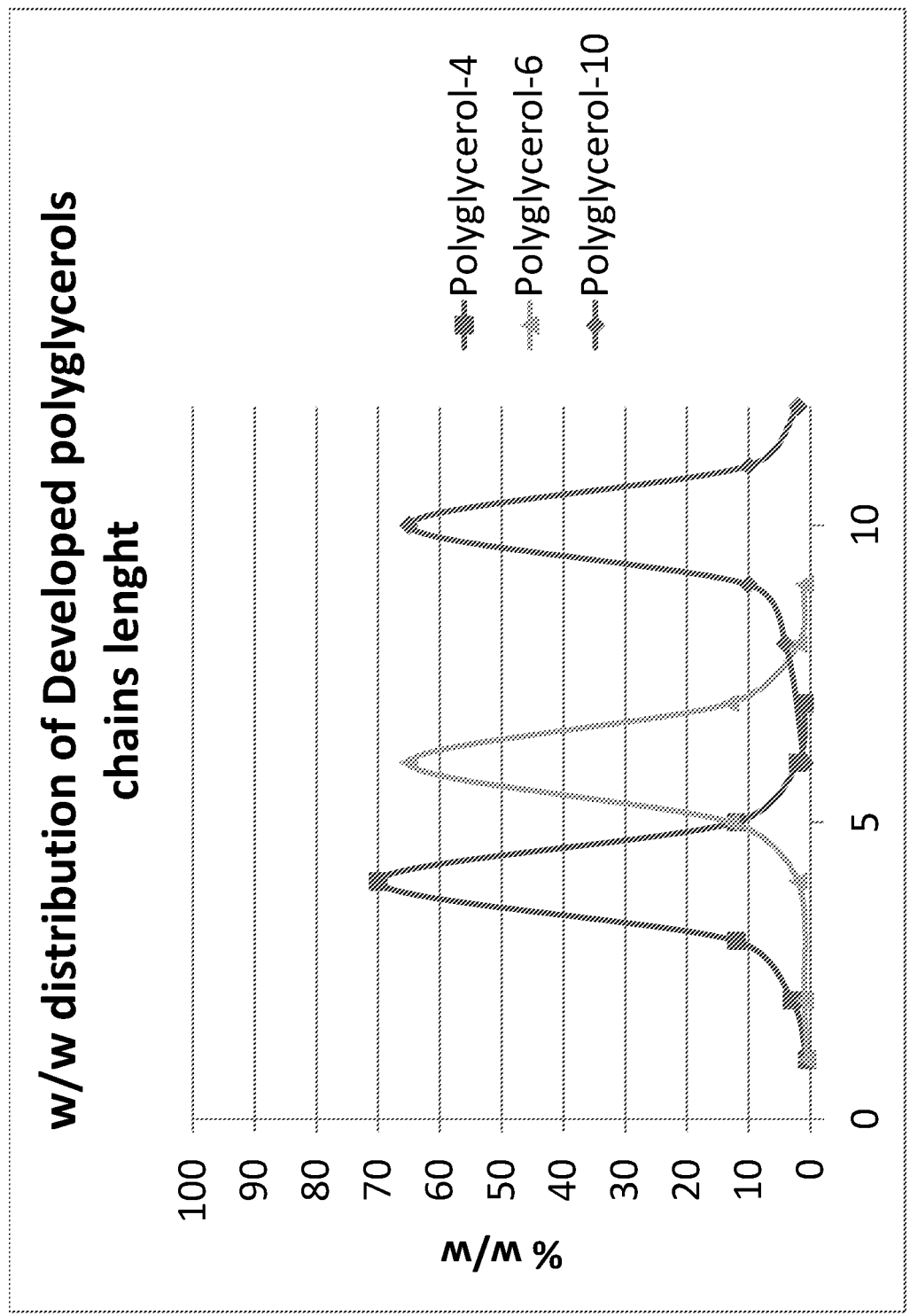
FIG. 2 shows the gaussian distribution of polyglycerols-2, -4 and -6 of the present disclosure.

Without being so limited, FIG. 2 illustrates the distribution of representative pure polyglycerols of different lengths of the instant disclosure (i.e. PG4, PG6 and PG10).

Fatty acids used for esterification reactions in accordance with the present disclosure, are fatty acids (consisting essentially of) of even chain lengths C8 to C14 chains, preferably C12 chains.

They are advantageously very pure, the remaining composition consisting of other fatty acid chain lengths. Although saturated fatty acids are advantageous in esterification reactions as they tend produce more stable and homogeneous esters (in the form of high melting point waxes or liquids) without the formation of a liquid/solid heterogeneous phase and are also constituents of the skin stratum corneum barrier unsaturated fatty acids esters may also be used.

In the context of "pure fatty acids", the term "pure" refers to a purity higher than that of commercially available C12-C14 fatty acid chains. It a specific embodiment, it refers to a purity of >85%w/w, preferably 90, most preferably 91, 92, 93, 94, 95, 96, 97, 98, 99 or 100% w/w. In a more specific embodiment, it refers to a purity of >95% w/w, and preferably >98% w/w.

PG6, PG4, PG10 and the fatty acid can be purified by any known method. For example, and without being so limited, the most used method is the column distillation used also in petrol-chemical. A high column with an oven on the bottom is putted under vacuum and the product to be distilled is fractionated by boiling points. The column has a temperature gradient that decreases from bottom to top, so that at the top are recovered purified low boiling point molecules and at the bottom are recovered purified high boiling point molecules. Alternatively, thin film evaporation performed under vacuum can be used. The method includes a heated surface (such as a rotating cylinder or a plane surface) with a thin film of a mix of the molecules to be purified (e.g., PGs or fatty acids). Near the thin film (between a few mm to a few cm of distance) is a cooled surface, that condenses the material that evaporates from the heated surface. By modulating the heating-vacuum balance, molecules (e.g., PGs) can be separated starting from those having low boiling points. Fatty acids are typically purified by column distillation, but pure fatty acids may also be purchased.

In some aspects, the present disclosure relates to emulsions (e.g., O/W emulsions), and other compositions produced from or comprising the liquids of the present disclosure. In some embodiments, the emulsions, and other compositions are stable for at least 1 week at 50° C. In some embodiments, the emulsions, and other compositions are stable for at least 2 weeks, 3 weeks or one month at 50° C. In some embodiments, the emulsions, and other compositions can comprise one or more preservatives (e.g., phenoxyethanol and parabens).

Process of Preparation

In another aspect, the present disclosure relates to a method for manufacturing the above-mentioned liquid, the method comprising mixing a pure polyglyceryl-6 and a pure polyglyceryl-X, wherein X is any integer any integer from 4-5 and 7-12 (e.g., a pure polyglyceryl-4 or a polyglyceryl-10) with fatty acid chains (e.g., C8-C18, specifically C10-C14, more specifically C12) to produce an esterification. The fatty acids can also be added as a second step after the polyglycerols have been mixed. Fatty acids can be of a single type or be a mixture of e.g., two types of fatty acids e.g., capric and lauric acids but are preferably of a single type (e.g., lauric) to optimize reproducibility of the emulsifier. The fatty acids are added at a concentration achieving a substitution of about 0.9 to about 1.5 hydroxyl group per polyglycerol molecule, preferably a substitution of about 1 hydroxyl group per polyglycerol molecule, namely about a 1:1 molar equivalent of polyglycerols vs fatty acid chain. In specific embodiments, the range of fatty acid: polyglycerol can be 1,5-2,3: 1-1,5 w/w.

In a specific embodiment, the polyglycerols and fatty acids are mixed at a temperature of between about 70 (or about 71, 72, 73, 74, 75, 76, 77, 78, 79, 80, 81, 82, 83, 84, 85, 86, 87, 88, 89, 90° C.) and 110 (or about 91, 92, 93, 94, 95, 96, 97, 98, 99, 100, 101, 102, 103, 104, 105, 106, 107, 108, 109); preferably at about 75 to about 105° C. or about 75 to about 100° C. or about 75 to about 95° C. or about 75 to about 90° C.; most preferably at about 90° C.

In a specific embodiment, the addition of the fatty acid is made in the presence of catalyst(s) suitable for esterification process. Suitable catalysts for use in the emulsifiers disclosed herein include any catalyst usable in the preparation of esters including but not limited to $H_2SO_4$, methanesulphonic acid (MSA), paratoluen sulphonic acid (PTSA), KOH, NaOH and other acid catalysts supported on solid base. They are optimally used because the esterification reaction is otherwise slow which may give rise to side reactions. In another specific embodiment, the esterification is performed at a temperature of between about 120° C. and about 170° C.

In specific embodiment, the duration is between about 30 minutes and about 2 hours, and preferably about 1 hour. Secondary reactions increase progressively with reactions times beyond 1 hour. The final mixture is thereafter cooled.

In specific embodiments, at least a part of the method (e.g., mixing polyglycerol and/or adding fatty acids and/or cooling) is performed in conditions preventing oxidation of the ingredients (e.g., under vacuum or under nitrogen atmosphere). In a specific embodiment, the conditions include vacuum nitrogen atmosphere. For example, the polyglycerols can be mixed with the fatty acids at between about 70 and 110° C., and prior to heating to produce the esterification, the conditions preventing oxidation are applied (e.g., vacuum or nitrogen atmosphere).

In other specific embodiments, the PG-X is PG-4. In such embodiment, the mixing step (i) mixes about 35 to about 45 parts of the polyglycerol-6 (and preferably about 40 parts) with about 55 to about 65 parts of the polyglycerol-4 (and preferably about 60 parts) to achieve preferably a PG6:PG4 ratio of about 40:60 w/w; and the adding step (ii) adds an amount of pure (e.g., C8-C14) fatty acid which achieves a substitution of about 0.9 to about 1.5 hydroxyl groups of the PGs (or to achieve a molar equivalent of about 0.9:1 to about 1.5:1 fatty acid chain: PGs). In specific embodiments, the ratio fatty acid: PGs (w/w) is of about 4,5-6,5: 8-12, in a specific embodiment 5.5:10. In such embodiments, the esterification temperature is preferably of about 140° C.

In other specific embodiments, the PG-X is PG-10. In such embodiment, the mixing step (i) mixes about 25 to about 35 parts of the polyglycerol-6 (and preferably about 30 parts) with about 65 to about 75 parts of the polyglycerol-10 (and preferably about 70 parts) to achieve preferably a PG6:PG10 ratio of about 30:70 w/w; and the adding step (ii) adds an amount of pure C8-C14 fatty acid which achieves a substitution of about 0.9 to about 1.5 hydroxyl groups of the PGs (or to achieve a molar equivalent of about 0.9:1 to about 1.5:1 fatty acid chain: PGs). In specific embodiments, the ratio fatty acid: PGs (w/w) is of about 25-35:65-75 more specifically about 30:70 w/w. In such embodiments, the esterification temperature is preferably of about 160° C.

Oil-in-Water Emulsion Preparation

O/W emulsions may be prepared with the above o/w emulsifiers using a cold or a hot process.

In a cold process, the O/W emulsion can be produced by first preparing an oil phase by melting/mixing the liquids of the present disclosure (e.g., 5% by weight) with a pharmaceutically or cosmetically acceptable oil (e.g., about 10% by weight) at room temperature (e.g., about 20° C. to about 30° C.), and mixing the oil phase with a water phase, which may also be at room temperature (e.g., about 20° C. to about 30° C.), and may optionally contain preservatives (e.g., phenoxyethanol and parabens) or other additives. The oil phase can be added to the water phase under stirring (e.g., using a homogenizer).

In a hot process, an O/W emulsion can be produced by first preparing an oil phase by melting/mixing the liquids of the present disclosure (e.g., 5% by weight) with a pharmaceutically or cosmetically acceptable oil (e.g., about 10% by weight) and heating (e.g., about 70° C. to about 75° C.), and mixing the oil phase with a water phase, which may also be heated (e.g., about 70° C. to about 75° C.), and may optionally contain preservatives (e.g., phenoxyethanol and parabens) or other additives. The oil phase can be added to the water phase under stirring (e.g., using a homogenizer).

In some embodiments, the oil phase can comprise any suitable oil components which are skin-compatible oil components or component mixtures that are non-water-mixable and which may, for example, be natural oils, fatty acid esters, mono-, di- or triglycerides, or other oils, or mixtures thereof. Preferably, the oils are liquid at ambient temperature, in particular are liquid at 20° C. or at 25° C. They can contain certain amounts of solid lipid components (e.g. fats) as long as the complete oily mixture is liquid at ambient temperature or at the temperatures mentioned above. Other oils which can be incorporated comprise natural oils or fats, or natural oil derivatives, in particular of vegetable origin. Examples are almond oil, soybean oil, sunflower oil, safflower oil, corn oil, canola oil, borage oil, evening primrose oil, grape seed oil, wheat germ oil, avocado oil, jojoba oil, kernel oil, sesame oil, walnut oil, linseed oil, palm oil, olive oil, macadamia oil, castor oil, rapeseed oil, peanut oil, coconut oil, and turnip seed oil.

Methods and Uses

In some embodiments, compositions (e.g., O/W emulsions) produced from or comprising liquids of the present disclosure can be used in topical products. For example, they can be used in cosmetic and/or pharmaceutical compositions.

Formulations and Additives

In some embodiments, the viscosity of the resulting oil-in-water emulsion can be about 100-20000 cPs. Advantageously, it can be between about 100 to about 1000 cPs, and more specifically between about 200 and 1000 cPs. Such low viscosity enables the use of these compositions for applications where liquid formulations are sought.

In some embodiments therefore, compositions of the present disclosure can be in the form of milks, serums, fluid lotions, and vaporizable/sprayable fluid lotions (sprays such as sunscreen sprays). The composition according to the present disclosure possesses appropriate fluidity characteristics to also serve for the impregnation of substrates consisting of synthetic or natural, woven or nonwoven textile fibers, or papers, for constituting articles, for example wipes, intended for care, protection or cleaning of the skin, of the scalp or of the hair, or for example papers for sanitary or household use.

In some embodiments, compositions of the present disclosure can be used by application on the skin, hair or scalp, whether it is direct application in the case of a cosmetic, dermo-cosmetic, dermo-pharmaceutical or pharmaceutical composition, or indirect application in the case of a product for the care, protection, or cleaning of the body, being in the form of a textile article, for example a wipe, or of paper, for example a paper for sanitary use, intended to be in contact with the skin, hair or scalp.

The present disclosure also relates to the cosmetic use of the composition as defined herein for cleaning, for protection and/or for care of the skin, hair or scalp. Compositions of the present disclosure can be used for care or for protection of the skin, for example as serums, milk, and lotions for care or for protection of the face, hands and body.

In some embodiments, compositions according to the present disclosure can also be used as a product for protecting the skin against the sun's rays, and as a skin make-up product. In a particular embodiment, compositions according to the present disclosure can include an ultraviolet absorber. Examples of the ultraviolet absorbers include benzoic acid ultraviolet absorbers such as p-aminobenzoic acid (hereinafter, abbreviated as "PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxycinnamate, cyclohexyl-p-methoxycinnamate, ethyl-.alpha.-cyano-.beta.-phenyl cinnamate, 2-ethylhexykalpha.-cyano-.beta.-phenyl cinnamate, and glycerylmono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethyl hexyl-4'-phenylbenzophenone-2-carboxylate, 2-hydroxy-4-n-octoxybenzophenone, and 4-hydroxy-3-carboxybenzophenone; 3-(4'-methyl benzylidene)-d,l-camphor; 3-benzylidene-d,l-camphor; urocanic acid; ethyl urocanate ester; 2-phenyl-5-methylbenzoxazole; 2,2'-hydroxy-5-methyl phenyl benzotriazole; 2-(2'-hydroxy-5'-t-octylphenyl)benzotriazole; 2-(2'-hydroxy-5'-methylphenyl) benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-p-(carbo-2'-ethylhexyl-1'-oxy)-1,3,5-triazine; and 4-tert-butyl-4'-methoxydibenzoylmethane. These ultraviolet absorbers may be used alone or in a combination of two or more thereof.

In some embodiments, compositions of the present disclosure can include a moisturizer. Examples of moisturizers include polyethylene glycol (PEG1500), propylene glycol, 1,3-propanediol, 3-methyl-1,3-butanediol, glycerol, 1,3-butylene glycol, xylitol, sorbitol, maltitol, chondroitin sulfuric acid, hyaluronic acid, mucoitin sulfuric acid, Trichosanthis semen acid, atelocollagen, cholesteryl-12-hydroxy stearate, sodium lactate, urea, bile salt, dl-pyrrolidone carboxylate, short-chain soluble collagen, diglycerin (EO) PO adducts, Rosa roxburghii extracts, yarrow extracts and melilot extracts. These moisturizers may be used alone or in a combination of two or more thereof.

In some embodiments, compositions of the present disclosure can include a thickener. Examples of thickeners include gum arabic, carrageenan, Karaya gum, gum tragacanth, carob gum, quince seed (marmelo), casein, dextrin, gelatin, sodium pectinate, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt-based cation-modified bentonite, quaternary ammonium salt-based cation-modified hectorite, and decaglycerin fatty acid ester eicosadioate condensate. These thickeners may be used alone or in a combination of two or more thereof.

In some embodiments, compositions of the present disclosure can include a preservative. Without being so limited, preservative are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben. These preservatives may be used alone or in a combination of two or more thereof.

In some embodiments, compositions of the present disclosure can include a pH adjuster. Examples of pH adjusters include edetic acid, disodium edetate, citric acid, sodium citrate, sodium hydroxide, potassium hydroxide, and triethanolamine. These pH adjusters may be used alone or in a combination of two or more thereof.

In some embodiments, compositions of the present disclosure can include a plant or algae extract. Examples of plant extracts include extracts of: aloe vera, artichoke, bamboo, bearberry, birch tree, borage, butcher's broom, capsicum, centella, chamomile, coffee, cucumber, devil's claw, dragonfruit, eucalyptus, fenugreek, flax, ginger, ginseng, grapefruit, green tea, Hamamelis, hawthorn, honeysuckle, hops, horse chestnut tree, horsetail, iris, jasmine, jojoba, kidney bean, kola, lavender, lemon, liquorice, lotus, magnolia tree, marshmallow, milk thistle, millet, myrrh tree, neem tree, noni tree, oat, olive tree, orchid, oregano, passion fruit, peppermint, pineapple, pomegranate tree, quinoa, raspberry bush, red clover, rice, rose, rose hips, rosemary, sage, saw palmetto, schizandra, sea fennel, sesame, strawberry, sunflower, thyme, tomato, turmeric, violet, walnut tree, watercress, wheat, white water lily, white willow, winter cherry, witch hazel, ylang-ylang, and yucca extracts. Examples of algae extracts include: bladderwrack, devil's apron, dulse, dunaliella, himanthalia, laminaria, pelvetia, porphyra, and spirulina extracts.

In some embodiments, compositions of the present disclosure can include an antioxidant. Examples of antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as .alpha.-carotone, .beta.-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, .alpha.-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as .alpha.-linolenic acid, linoleic acid, oleic acid, folic acid and derivatives thereof, ubiquinone and ubiquinol and derivatives thereof, vitamin C and derivatives thereof such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, .alpha.-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as ZnO, $ZnSO_4$, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, ascorbir stearate, butyl hydroxyanisole, and gallic esters. These antioxidants may be used alone or in a combination of two or more thereof.

In some embodiments, compositions of the present disclosure can include chelating agents or sequestering agents (sequestrants). Examples of chelating agents include EDTA, disodium EDTA, trisodium EDTA, EGTA, disodium EGTA, trisodium EGTA, citric acid, phosphoric acid, and succinic acid.

In some embodiments, compositions of the present disclosure can include opacifying agents. Examples of pacifying agents include higher fatty alcohols such as cetyl, stearyl, cetostearyl alcohol, arachidyl and behenyl alcohols, solid esters such as cetyl palmitate, glyceryl laurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide or other sunblocking agents.

In some embodiments, compositions of the present disclosure can include one or more further topically active ingredients useful in skincare. Such active ingredients may include one or more of the following: antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin; antiviral compounds, for example selected from acyclovir, tamvir, and penciclovir; antifungal compounds, for example selected from the following: framesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc; anthelmintic compounds, for example metronidazole.

In some embodiments, compositions of the present disclosure can include a fragrance. Examples of fragrance include plant perfumes such as rose oil, jasmine oil, and lavender oil; and synthetic perfumes such as limonene, citral, linalool, and eugenol. These perfumes may be used alone or in a combination of two or more thereof.

Active and functional ingredients for use in compositions of the present disclosure, including those listed above, may be plant extracts, algae extracts, fruit extracts, vegetable extracts, leguminous plant extracts, ferments, proteolytic hydrolysates, peptides, yeast extracts and its derivatives, microorganism extracts, animal derivative extracts and/or synthetic compounds.

The present disclosure is illustrated in further details by the following non-limiting examples.

EXAMPLE 1

Preparation of pure PG4, pure PG6, pure PG10 and Pure Lauric Acid

Pure PG4, pure PG6, pure PG10 and pure lauric acid used in the preparation of the esters of Examples 2 to 6 below and tested in Examples 7 to 9 below were prepared as follows.

Commercial grades PG4, PG6 and PG10 were purchased from Inovym.

Inovym PG4 Composition Table:

|  | Molecular weight | % w/w commercially available PG4 |
| --- | --- | --- |
| Glycerol | 92.02 | <1% |
| Diglycerol (polyglycerol-2) | 166.18 | 5-6% |
| Triglycerol (polyglycerol-3) | 240.27 | 40-45% |
| Tetraglycerol (polyglycerol-4) | 314.36 | 25-30% |
| Pentaglycerol (polyglycerol-5) | 388.45 | 10-15% |
| Hexaglycerol (polyglycerol-6) | 462.54 | 3-6% |
| Heptaglycerol (polyglycerol-7) | 536.63 | 2-5% |
| Octaglycerol (polyglycerol-8) | 610.72 | <1% |

Inovym PG6 Composition Table:

|  | Molecular weight | % w/w commercially available PG6 |
| --- | --- | --- |
| Glycerol | 92.02 | <1% |
| Diglycerol (polyglycerol-2) | 166.18 | 4-6% |
| Triglycerol (polyglycerol-3) | 240.27 | 22-28% |
| Tetraglycerol (polyglycerol-4) | 314.36 | 20-25% |
| Pentaglycerol (polyglycerol-5) | 388.45 | 13-18% |
| Hexaglycerol (polyglycerol-6) | 462.54 | 10-15% |
| Heptaglycerol (polyglycerol-7) | 536.63 | 4-8% |
| Octaglycerol (polyglycerol-8) | 610.72 | 4-6% |
| Nonaglycerol and higher >721.9 | >721.9 | 12-15% |

Inovym PG10 Composition Table:

|  | Molecular weight | % w/w commercially available PG10 |
| --- | --- | --- |
| Glycerol | 92.02 | <1% |
| Diglycerol (polyglycerol-2) | 166.18 | 4-6% |
| Triglycerol (polyglycerol-3) | 240.27 | 10-14% |
| Tetraglycerol (polyglycerol-4) | 314.36 | 12-16% |
| Pentaglycerol (polyglycerol-5) | 388.45 | 11-15% |
| Hexaglycerol (polyglycerol-6) | 462.54 | 8-12% |
| Heptaglycerol (polyglycerol-7) | 536.63 | 7-11% |
| Octaglycerol (polyglycerol-8) | 610.72 | 5-7% |
| Nonaglycerol and higher >721.9 | >721.9 | 30-35% |

These PGs were purified using thin film vacuum distillation as described above.

Commercial grade lauric acid was purchased from ICOF Europe GmbH.

| Fatty acids | % w/w ICOF Europe GmbH Lauric acid |
| --- | --- |
| Caprylic acid (C8) | 6-8% |
| Decanoic acid (C10) | 6-12% |
| Lauric acid (C12) | 45-55% |
| Myristic acid (C14) | 12-20% |
| Palmitic acid (C16) | 8-12% |
| Oleic acid (C18:1) | 4-8% |
| Other | <5% |

The purchased lauric acid was purified using vacuum column distillation as described above.

EXAMPLE 2

Emulsifier A: PG4 and PG6 Laurate

Under nitrogen, about 60 g of pure PG4 (PG4 minimum content about 70% w/w) from were mixed at about 90° C. with about 40 g of pure PG6 (PG6 minimum content about 65% w/w)—Ratio 60:40/PG4:PG6. Then, 55 g of pure lauric acid (minimum content of about 98% w/w) were added and melted in the PG mixtures. $H_2SO_4$ 90%, a catalyst for the esterification, was added and the mixture was heated up to about 140° C. for about 1 h. The final mixture was cooled down and discharged.

EXAMPLE 3

Emulsifier B: PG6 and PG10 Laurate

Under nitrogen, about 70 g of the pure PG6 (PG6 minimum content about 65% w/w) was mixed at about 90° C. with about 30 g of the pure PG10 (PG10 minimum content about 65% w/w)—Ratio 70:30/PG6:PG10. About 37.8 g of the pure lauric acid (minimum content of about 98% w/w) was added and melted in the PG mixtures. $H_2SO_4$ 90%, a catalyst for the esterification, was added and the mixture was heated up to about 160° C. for about 1 h. The final mixture was cooled down and discharged.

EXAMPLE 4

PG4 Laurate Prepared with Pure PG4 and Pure Laurate

Under nitrogen, about 100 g of pure polyglycerol-4 was mixed at about 90° C. with about 63.7 g of pure lauric acid (minimum content of at least about 98% w/w lauric acid). H$_2$SO$_4$ 90%, a catalyst for the esterification, was added and the mixture was heated up to about 140° C. for about 1 h. The final mixture was cooled down and discharged.

EXAMPLE 5

PG6 Laurate Prepared with Pure PG6 and Pure Laurate

Under nitrogen, about 100 g of pure polyglycerol-6 was mixed at about 90° C. with about 43.3 g of pure lauric acid (minimum content of at least about 98% w/w lauric acid). H$_2$SO$_4$ 90%, a catalyst for the esterification, was added and the mixture was heated up to about 140° C. for about 1 h. The final mixture was cooled down and discharged.

EXAMPLE 6

PG10 Laurate Prepared with Pure PG10 and Pure Laurate

Under nitrogen, about 100 g of the pure polyglycerol-10 was mixed at about 90° C. with about 26 g of the pure lauric acid (minimum content of at least about 98% w/w lauric acid). H$_2$SO$_4$ 90%, a catalyst for the esterification, was added and the mixture was heated up to about 160° C. for about 1 h. The final mixture was cooled down and discharged.

EXAMPLE 7

PG4 Laurate Prepared with Commercially Available PG4 and Purified Laurate

Under nitrogen, about 100 g of commercially available polyglycerol-4 was mixed at about 90° C. with about 61.8 g of pure lauric acid (minimum content of at least about 98% w/w lauric acid). H$_2$SO$_4$ 90%, a catalyst for the esterification, was added and the mixture was heated up to about 140° C. for about 1 h. The final mixture was cooled down and discharged.

EXAMPLE 8

PG6 Laurate Preparation with Commercially Available PG4 and Purified Laurate Under nitrogen, about 100 g of commercially available polyglycerol-6 was mixed at about 90° C. with about 37.4 g of pure lauric acid (minimum content of at least about 98% w/w lauric acid). H$_2$SO$_4$ 90%, a catalyst for the esterification, was added and the mixture was heated up to about 140° C. for about 1 h. The final mixture was cooled down and discharged.

EXAMPLE 9

PG10 Laurate Preparation with Commercially Available PG10 and Purified Laurate Under nitrogen, about 100 g of commercially available polyglycerol-10 was mixed at about 90° C. with about 26 g of pure lauric acid (minimum content of at least about 98% w/w lauric acid). H$_2$SO$_4$ 90%, a catalyst for the esterification, was added and the mixture was heated up to about 160° C. for about 1 h. The final mixture was cooled down and discharged.

EXAMPLE 10

PG4 Laurate PG6 Laurate Prepared with Commercially Available PG4 and PG6 Mixed before Esterification Under nitrogen, about 60 g of commercially available PG4 were mixed at about 90° C. with about 40 g of commercially available PG6—Ratio 60:40/PG4:PG6. Then, 52 g of pure lauric acid (minimum content of about 98% w/w) were added and melted in the PG mixtures. H$_2$SO$_4$ 90%, a catalyst for the esterification, was added and the mixture was heated up to about 140° C. for about 1 h. The final mixture was cooled down and discharged.

EXAMPLE 11

PG6 Laurate PG10 Laurate Prepared with Commercially Available PG4 and PG10 Mixed before Esterification Under nitrogen, about 70 g of commercially available PG6 was mixed at about 90° C. with about 30 g of commercially available PG10—Ratio 70:30/PG6:PG10. About 35.8 g of pure lauric acid (minimum content of about 98% w/w) was added and melted in the PG mixtures. H$_2$SO$_4$ 90%, a catalyst for the esterification, was added and the mixture was heated up to about 160° C. for about 1 h. The final mixture was cooled down and discharged.

EXAMPLE 12

Stability of Emulsions Prepared using a Cold Process (Prepared at 25° C.)

Phase A and phase C were prepared separately and stirred at room temperature (20° C.-30° C.) Phase B was dispersed in phase A under agitation. Phase C was added to phase A±B, under agitation and the mixture was homogenized for a few minutes. Phase D was added under gentle stirring and the pH adjusted if needed.

| INCI NAME | % w/w | Function |
|---|---|---|
| PHASE A | | |
| Water (Aqua) | up to 100.00 | |
| Glycerin | 3.00 | Humectant |
| PHASE B | | |
| Aerylates/C10-30 Alkyl Acrylate Crosspolymer | 0.10 | Thickener |
| PHASE C | | |
| ONE OF EMULSIFIERS A TO L | 5.00 | Emulsifier |
| *Prunus Amigdalus Dulcis* (Sweet Almond) Oil | 5.00 | Emollient |
| Caprylic/Capric Triglyceride | 3.00 | Emollient |
| Paraffinum Liquidum | 2.00 | Emollient |

| INCI NAME | % w/w | Function |
|---|---|---|
| PHASE D | | |
| Phenoxyethanol, Methylparaben, Butylparaben, Ethylparaben, Ethylparaben, Propylparaben | a.n. | Preservative |
| Dew ™ | a.n. | Perfume |
| VISCOSITY after 24 h Brk, RVDV-I Prime, Sp 03, 20 rpm | 1000-1200 cps | |
| pH (100%) | 5.0-7.0 | |

The stability of the emulsions prepared with each of the emulsifiers noted in the table immediately below was tested by exposing each of them to a temperature of 50° C. in an oven for one month in a closed container. Every week a visual check was performed to determine whether there was any water/oil separation. If no separation was detected, a viscosity and pH checks were performed. An emulsion was considered unstable if the visual test showed any kind of separation before the 4-week period.

| | Stability | Week 1 | Week 2 | Week 3 | Week 4 | Week 5 |
|---|---|---|---|---|---|---|
| A | Emulsifier A (Example 2) | Stable | Stable | Stable | Stable | Stable |
| B | Emulsifier B (Example 3) | Stable | Stable | Stable | Stable | Stable |
| C | Polyglyceryl-4 Laurate prepared with commercially available PG4 (Example 7) | Stable | Unstable | / | / | / |
| D | Polyglyceryl-6 Laurate prepared with commercially available PG6 (Example 8) | Unstable | / | / | / | / |
| E | Polyglyceryl-10 Laurate prepared with commercially available PG10 (Example 9) | Unstable | / | / | / | / |
| F | PG4 laurate and PG6 laurate prepared mixing commercially PG4 and PG6 60:40 before esterification (Example 10) | Stable | Unstable | / | / | / |
| G | PG6 laurate and PG10 laurate prepared mixing commercially PG6 and PG10 70:30 before esterification (Example 11) | Unstable | / | / | / | / |
| H | Mixture of Example 4 and Example 5 esters (60:40) | Unstable | / | / | / | / |
| I | Mixture of Example 5 and Example 6 esters (70:30) | Unstable | / | / | / | / |
| L | Pure PG4 Laurate (Example 4) | Stable | Stable | Unstable | / | / |
| M | Pure PG6 Laurate (Example 5) | Stable | Unstable | / | / | / |
| N | Pure PG10 Laurate (Example 6) | Stable | Unstable | / | / | / |

EXAMPLE 13

Stability of Emulsions Prepared using a Cold Process

Phase A was prepared and phase B was dispersed in Phase B under agitation at about 20-30° C. The mixture was then homogenized for a few minutes. Phase C was added and the resulting mixture was homogenized until complete powder dispersion. Phase D was added and the resulting mixture was homogenized for a few minutes. The ingredients of phase E were then added one by one in the noted order under gentle stirring.

| INCI NAME | % w/w | Function |
|---|---|---|
| PHASE A | | |
| Water (Aqua) | up to 100.00 | |
| Glycerin | 3.00 | Humectant |
| PHASE B | | |
| ONE OF EMULSIFIERS A TO L | 5.00 | Emulsifier |
| PHASE C | | |
| Xanthan Gum | 0.50 | Thickener |
| Tapioca Starch | 1.00 | Thickener - Sensorial Modifier |
| PHASE D | | |
| Oryza Sativa Bran Oil | 2.50 | Emollient |
| Gossypium Herbaceum Seed Oil | 2.50 | Emollient |
| Octyldodecyl Oleate (and) Octyldodecyl Stearoyl Stearate (and) Polyhydroxystearic Acid (and) Octyldodecanol | 3.00 | Emollient |
| Caprylic/Capric Triglyceride | 2.00 | Emollient |
| PHASE E | | |
| Phenoxyethanol, Methylparaben, Butylparaben, Ethylparaben, Propylparaben | a.n. | Preservative |
| Dew ™ | a.n. | Perfume |
| VISCOSITY after 24 h Brk, RVDV-I Prime, Sp 03, 20 rpm | 1000-1100 cps | |
| pH (100%) | 5.0-7.0 | |

The stability of the emulsions prepared with each of the emulsifiers noted in the table immediately below was tested by exposing each of them to a temperature of 50° C. in an oven for one month in a closed container. Every week a visual check was performed to determine whether there was any water/oil separation. If no separation was detected, a viscosity and pH checks were performed. An emulsion was considered unstable if the visual test showed any kind of separation before the 4-week period.

|   | Stability | Week 1 | Week 2 | Week 3 | Week 4 | Week 5 |
|---|---|---|---|---|---|---|
| A | Emulsifier A (Example 2) | Stable | Stable | Stable | Stable | Stable |
| B | Emulsifier B (Example 3) | Stable | Stable | Stable | Stable | Stable |
| C | Polyglyceryl-4 Laurate prepared with commercially available PG4 (Example 7) | Unstable | / | / | / | / |
| D | Polyglyceryl-6 Laurate prepared with commercially available PG6 (Example 8) | Stable | Unstable | / | / | / |
| E | Polyglyceryl-10 Laurate prepared with commercially available PG10 (Example 9) | Unstable | / | / | / | / |
| F | PG4 laurate and PG6 laurate prepared mixing commercially available PG4 and PG6 60:40 before esterification (Example 10) | Stable | Unstable | / | / | / |
| G | PG6 laurate and PG10 laurate prepared mixing commercially available PG6 and PG10 70:30 before esterification (Example 11) | Unstable | / | / | / | / |
| H | Mixture of Example 4 and Example 5 esters (60:40) | Unstable | / | / | / | / |
| I | Mixture of Example 5 and Example 6 esters (70:30) | Unstable | / | / | / | / |
| L | Pure PG4 Laurate (Example 4) alone | Stable | Unstable | / | / | / |
| M | Pure PG6 Laurate (Example 5) alone | Stable | Unstable | / | / | / |
| N | Pure PG10 Laurate (Example 6) alone | Unstable | / | / | / | / |

EXAMPLE 14

Emulsion Prepared with Hot Process

Phases $A_1$ and B were prepared, and each were heated up to about 75-80° C. Phase Ai was added to B very slowly under agitation. The mixture was cooled down to 25° C. under gentle stirring. Phase A was added under gentle stirring and then phase C was added under gentle stirring.

| INCI NAME | % w/w | Function |
|---|---|---|
| PHASE A | | |
| Water (Aqua) | Up to 100.00 | |
| PHASE $A_1$ | | |
| Water (Aqua) | 20.00 | |
| PHASE B | | |
| ONE OF EMULSIFIERS A TO L | 5.00 | Emulsifier |
| Dicaprylyl Ether | 1.00 | Emollient |
| Phenoxyethanol, Ethylhexylglycerin | a.n. | Preservative |
| PHASE C | | |
| Polysorbate 20 | a.n. | Solubilizer |
| Dew | a.n. | Parfum |
| VISCOSITY after 24 h Brk, RVDV-I Prime, Sp 03, 20 rpm | 200-300 cps | |
| (pH (100%) | 5.0-7.0 | |

The stability of the emulsions prepared with each of the emulsifiers noted in the table immediately below was tested by exposing each of them to a temperature of 50° C. in an oven for one month in a closed container. Every week a visual check was performed to determine whether there was any water/oil separation. If no separation was detected, a viscosity and pH checks were performed. An emulsion was considered unstable if the visual test showed any kind of separation before the 4-week period.

|   | Stability | Week 1 | Week 2 | Week 3 | Week 4 | Week 5 |
|---|---|---|---|---|---|---|
| A | Emulsifier A (Example 2) | Stable | Stable | Stable | Stable | Stable |
| B | Emulsifier B (Example 3) | Stable | Stable | Stable | Stable | Stable |
| C | Polyglyceryl-4 Laurate prepared with commercially available PG4 (Example 7) | Unstable | / | / | / | / |
| D | Polyglyceryl-6 Laurate prepared with commercially available PG6 (Example 8) | Unstable | / | / | / | / |
| E | Polyglyceryl-10 Laurate prepared with commercially available PG10 (Example 9) | Stable | Unstable | / | / | / |
| F | PG4 laurate and PG6 laurate prepared mixing commercial PG4 and PG6 60:40 before esterification (Example 10) | Stable | Unstable | / | / | / |
| G | PG6 laurate and PG10 laurate prepared mixing commercial PG6 and PG10 70:30 before esterification (Example 11) | Stable | Unstable | / | / | / |
| H | Simple Mixture of Example 4 and Example 5 esters (60:40) | Unstable | / | / | / | / |
| I | Simple Mixture of Example 5 and Example 6 esters (70:30) | Unstable | / | / | / | / |
| L | Pure PG4 Laurate (Example 4) alone | Unstable | / | / | / | / |
| M | Pure PG6 Laurate (Example 5) alone | Stable | Unstable | / | / | / |
| N | Pure PG10 Laurate (Example 6) alone | Stable | Unstable | / | / | / |

The invention claimed is:

1. An oil-in-water (O/W) emulsifier consisting essentially of esters of polyglycerol-6 and of a C12-C14 fatty acid, and of polyglycerol-X, wherein X is any one of 4, 5 and 7 to 12 and of the C12-C14 fatty acid,
   wherein the esters were prepared by mixing the polyglycerol-6 and the polyglycerol-X prior to esterification with the C12-C14 fatty acid,
   wherein prior to mixing the C12-C14 fatty acid with the polyglycerols, the C12-C14 fatty acid has a purity of at least 85% w/w, and the polyglycerols have a purity of at least 60% w/w, and
   wherein the emulsifier can form a stable O/W emulsion for at least 1 month at about 50° C., and wherein the emulsifier is liquid at about 20° C. to about 30° C.

2. The emulsifier of claim 1, wherein the polyglycerol-X is a polyglycerol-4 and wherein the ratio of the esters of polyglycerols in the emulsifier is:
   i. about 35 to about 45 parts of the ester of the polyglycerol-6 or about 40 parts of the ester of the polyglycerol-6; for
   ii. about 55 to about 65 parts of the ester of the polyglycerol-4 or about 60 parts of the ester of the polyglycerol-4.

3. The emulsifier of claim 2, wherein prior to mixing the polyglycerol-4 with the C12-C14 fatty acid, the polyglycerol-4 has a purity of at least 70% w/w.

4. The emulsifier of claim 1, wherein the polyglycerol-X is a polyglycerol-10 and wherein the ratio of the esters of polyglycerols in the emulsifier is:
   i. about 25 to about 35 parts of the ester of the polyglycerol-6 or about 30 parts of the ester of the polyglycerol-6; for
   ii. about 65 to about 75 parts of the ester of the polyglycerol-10 or about 70 parts of the ester of the polyglycerol-10.

5. The emulsifier of claim 4, wherein prior to mixing the polyglycero-10 with the C12-C14 fatty acid, the polyglycerol-10 has a purity of at least 65% w/w.

6. The emulsifier of claim 1, wherein the C12-C14 fatty acid has a length of (i) C14; or (ii) C12.

7. The emulsifier of claim 6, wherein the C12-C14 fatty acid is lauric acid.

8. The emulsifier of claim 1, wherein prior to mixing the C12-C14 fatty acid with the polyglycerols, the C12-C14 fatty acid has a purity of at least 98% w/w.

9. The emulsifier of claim 1, wherein the emulsifier comprises (i) between about 0.9 and about 1.5 equivalent C12-C14 fatty acid for about 1 equivalent polyglycerol; or (ii) about 1.0 equivalent C12-C14 fatty acid for about 1.0 equivalent polyglycerol.

10. The emulsifier of claim 1, wherein the emulsifier is present in an O/W emulsion.

11. The emulsifier of claim 10, wherein the emulsion does not comprise a co-emulsifier, a polar or an ionic surfactant, an ethoxylated product, a propoxylated product, a rheological modifier, a gelling agent, or any combination thereof.

12. The emulsifier of claim 10, wherein the emulsion is a cosmetic liquid composition.

13. The emulsifier of claim 10, wherein the emulsion has a viscosity between 100 and 1200 cPs.

14. A method of preparing an oil-in-water (O/W) emulsifier comprising:
   (a) heating polyglycerol-6, polyglycerol-X, wherein X is any one of 4, 5 and 7 to 12, and a C12-C14 fatty acid at about 70° C. to about 110° C. to form a mixture, wherein prior to mixing the C12-C14 fatty acid with the polyglycerols, the polyglycerols have a purity of at least 60% w/w, and the C12-C14 fatty acid has a purity of at least 85% w/w; and
   (b) esterifying the mixture at a temperature between about 120 and about 170° C., wherein the O/W emulsifier consists essentially of esters of the polyglycerol-6 and of the C12-C14 fatty acid, and of polyglycerol-X and of the C12-C14 fatty acid; and the emulsifier can form a stable O/W emulsion for at least 1 month at about 50° C., and wherein the emulsifier is liquid at about 20° C. to about 30° C.

15. The method of claim 14, wherein the polyglycerol-X is a polyglycerol-4 and wherein the ratio of the esters of polyglycerols in (a) is:
   i. about 35 to about 45 parts of the ester of polyglycerol-6 or about 40 parts of the ester of the polyglycerol-6; for
   ii. about 55 to about 65 parts of the ester of the polyglycerol-4 or about 60 parts of the ester of the polyglycerol-4.

16. The method of claim 15, wherein prior to mixing the polyglycerol-4 with the C12-C14 fatty acid, the polyglycerol-4 has a purity of at least 70% w/w.

17. The method of claim 14, wherein the polyglycerol-X is a polyglycerol-10 and wherein the ratio of the ester of polyglycerols in (a) is:
   i. about 25 to about 35 parts of the ester of the polyglycerol-6 or about 30 parts of the ester of the polyglycerol-6; for
   ii. about 65 to about 75 parts of the ester of the polyglycerol-10 or about 70 parts of the ester of the polyglycerol-10.

18. The method of claim 17, wherein prior to mixing the polyglycerol-10 with the C12-C14 fatty acid, the polyglycerol-10 has a purity of at least 65% w/w.

19. The method of claim 14, wherein the C12-C14 fatty acid has a length of (i) C14; or (ii) C12.

20. The method of claim 19, wherein the C12-C14 fatty acid is lauric acid.

21. The method of claim 14, wherein prior to mixing the C12-C14 fatty acid with the polyglycerols, the C12-C14 fatty acid has a purity of at least 98% w/w.

22. The method of claim 14, wherein there is (i) between about 0.9 and about 1.5 equivalent C12-C14 fatty acid for about 1 equivalent polyglycerol in the mixture; or (ii) about 1.0 equivalent C12-C14 fatty acid for about 1.0 equivalent polyglycerol in the mixture.

23. A composition comprising the emulsifier of claim 1, and at least one further pharmaceutically or cosmetically acceptable ingredient.

* * * * *